(12) United States Patent
Blaustein et al.

(10) Patent No.: US 11,655,570 B2
(45) Date of Patent: *May 23, 2023

(54) ILLUMINATED GARMENT

(71) Applicant: Biothread LLC, Wayne, PA (US)

(72) Inventors: Lawrence A. Blaustein, Chagrin Falls, OH (US); Jay Tapper, Wayne, PA (US); Jaleh Factor, Manhattan Beach, CA (US); Boris Kontorovich, Brooklyn, NY (US); Jens Johnson, Austin, TX (US); Daniel Shuter, New York, NY (US)

(73) Assignee: BIOTHREAD LLC, Wayne, PA (US)

( * ) Notice: Subject to any disclaimer, the term of this patent is extended or adjusted under 35 U.S.C. 154(b) by 761 days.

This patent is subject to a terminal disclaimer.

(21) Appl. No.: 16/596,246

(22) Filed: Oct. 8, 2019

(65) Prior Publication Data

US 2021/0100296 A1    Apr. 8, 2021

(51) Int. Cl.
*D04B 1/24* (2006.01)
*A61N 5/06* (2006.01)
(Continued)

(52) U.S. Cl.
CPC ............. *D04B 1/26* (2013.01); *A41D 27/085* (2013.01); *A61N 5/0622* (2013.01); *D04B 1/243* (2013.01); *A41B 9/02* (2013.01); *A41B 2400/32* (2013.01); *A61N 5/0613* (2013.01); *A61N 2005/063* (2013.01); *A61N 2005/0645* (2013.01); *A61N 2005/0659* (2013.01);
(Continued)

(58) Field of Classification Search
CPC ........ D10B 2401/18; D10B 2403/0243; D10B 2403/02431; D10B 2401/20; D04B 1/123; D04B 1/243; D04B 1/28; A61N 5/0622; A61N 5/0613; A61N 2005/063; A61N 2005/0645; A61N 2005/0659; A61N 2005/0662; Y10T 442/40; Y10T 442/30; A41D 13/01; A41D 27/085; A41B 9/02; A41B 2400/32
See application file for complete search history.

(56) References Cited

U.S. PATENT DOCUMENTS 4,234,907 A    11/1980   Daniel
4,727,603 A     3/1988   Howard
(Continued)

FOREIGN PATENT DOCUMENTS

CN    206535008 U  * 10/2017
EP      3396038 A1 * 10/2018  ............. D04B 21/14
(Continued)

OTHER PUBLICATIONS

International Search Report filed in PCT/US2020/053883 dated Jan. 5, 2021.

*Primary Examiner* — Jennifer A Steele
(74) *Attorney, Agent, or Firm* — Rankin, Hill & Clark LLP

(57) ABSTRACT

An illuminated garment includes a base layer having knitted looped threads that hold in position a plurality of optical fibers. The optical fibers are laid into the base layer during the same knitting cycle as the base layer and are configured to emit light through the respective sides of the optical fibers and along the length of each optical fiber in response to receiving light from a light source through at least one end of the respective optical fibers.

5 Claims, 4 Drawing Sheets

(51) Int. Cl.
  *D04B 1/26*    (2006.01)
  *A41B 9/02*    (2006.01)
  *A41D 27/08*   (2006.01)
  *D04B 11/28*   (2006.01)
  *D03D 15/547*  (2021.01)

(52) U.S. Cl.
  CPC .... *A61N 2005/0662* (2013.01); *D03D 15/547* (2021.01); *D04B 11/28* (2013.01); *D10B 2401/18* (2013.01); *D10B 2403/0243* (2013.01); *D10B 2403/02431* (2013.01)

(56) References Cited

U.S. PATENT DOCUMENTS

| | | | |
|---|---|---|---|
| 4,761,047 | A | 8/1988 | Mori |
| 5,813,148 | A | 9/1998 | Guerra |
| 6,145,551 | A | 11/2000 | Jayaraman |
| 6,341,504 | B1 | 1/2002 | Istook |
| 8,214,008 | B2 | 7/2012 | Hassonjee et al. |
| 8,428,686 | B2 | 4/2013 | Kuo et al. |
| 8,621,891 | B2 | 1/2014 | Dua et al. |
| 8,709,185 | B2 | 4/2014 | Hassonjee et al. |
| 2002/0138120 | A1 | 9/2002 | Whitehurst |
| 2003/0167080 | A1 | 9/2003 | Hart et al. |
| 2004/0204639 | A1 | 10/2004 | Casciani |
| 2006/0221596 | A1 | 10/2006 | Chang |
| 2006/0257095 | A1* | 11/2006 | Walt .................. A61B 5/6804 385/901 |
| 2007/0288071 | A1 | 12/2007 | Rogers |
| 2008/0253712 | A1* | 10/2008 | Allen .................. D03D 15/283 385/12 |
| 2009/0034236 | A1 | 2/2009 | Reuben |
| 2009/0291606 | A1 | 11/2009 | Malhomme et al. |
| 2010/0029157 | A1 | 2/2010 | Brochier et al. |
| 2010/0053990 | A1 | 3/2010 | Brochier et al. |
| 2010/0114263 | A1 | 5/2010 | Pressler |
| 2010/0249557 | A1 | 9/2010 | Besko |
| 2011/0176326 | A1 | 7/2011 | Stephan |
| 2014/0070957 | A1 | 3/2014 | Longinotti-Buitoni et al. |
| 2014/0303693 | A1 | 10/2014 | Haarlander et al. |
| 2015/0177423 | A1* | 6/2015 | Scipioni .............. A41D 13/005 428/221 |
| 2016/0074547 | A1 | 3/2016 | Dobrinsky |
| 2016/0122911 | A1* | 5/2016 | Franz ................. D03D 15/41 139/420 C |
| 2016/0338644 | A1* | 11/2016 | Connor ............... A61B 5/1126 |
| 2017/0342607 | A1 | 11/2017 | Yamada |
| 2019/0133241 | A1 | 5/2019 | Chou |
| 2019/0374792 | A1* | 12/2019 | Tapper ................ D02G 3/441 |

FOREIGN PATENT DOCUMENTS

| | | | |
|---|---|---|---|
| WO | 2011/082420 | | 7/2011 |
| WO | 2014071898 | | 5/2014 |
| WO | WO-2016097524 A1 * | 6/2016 | .............. D04B 21/14 |
| WO | 2017/120367 | | 7/2017 |
| WO | 2019/178017 | | 9/2019 |

\* cited by examiner

ILLUMINATED GARMENT

BACKGROUND

Clothing made from light emitting fabrics is described in U.S. Pat. No. 4,234,907. This patent, however, describes such clothing as a fad item or as safety clothing to emit light outward when the wearer wishes to be seen.

US 2007/0089800 A1 discloses garment systems that include an integrated infrastructure for monitoring vital signs of an individual and for other monitoring purposes. Neither of the aforementioned patent documents discloses a garment for delivering therapeutic light toward the wearer.

SUMMARY

In view of the foregoing, an illuminated garment includes a base layer having knitted looped threads that hold in position a plurality of optical fibers. The optical fibers are laid into the base layer during the same knitting cycle as the base layer and are configured to emit light through the respective sides of the optical fibers and along the length of each optical fiber in response to receiving light from a light source through at least one end of the respective optical fiber.

DETAILED DESCRIPTION

Figure 1:
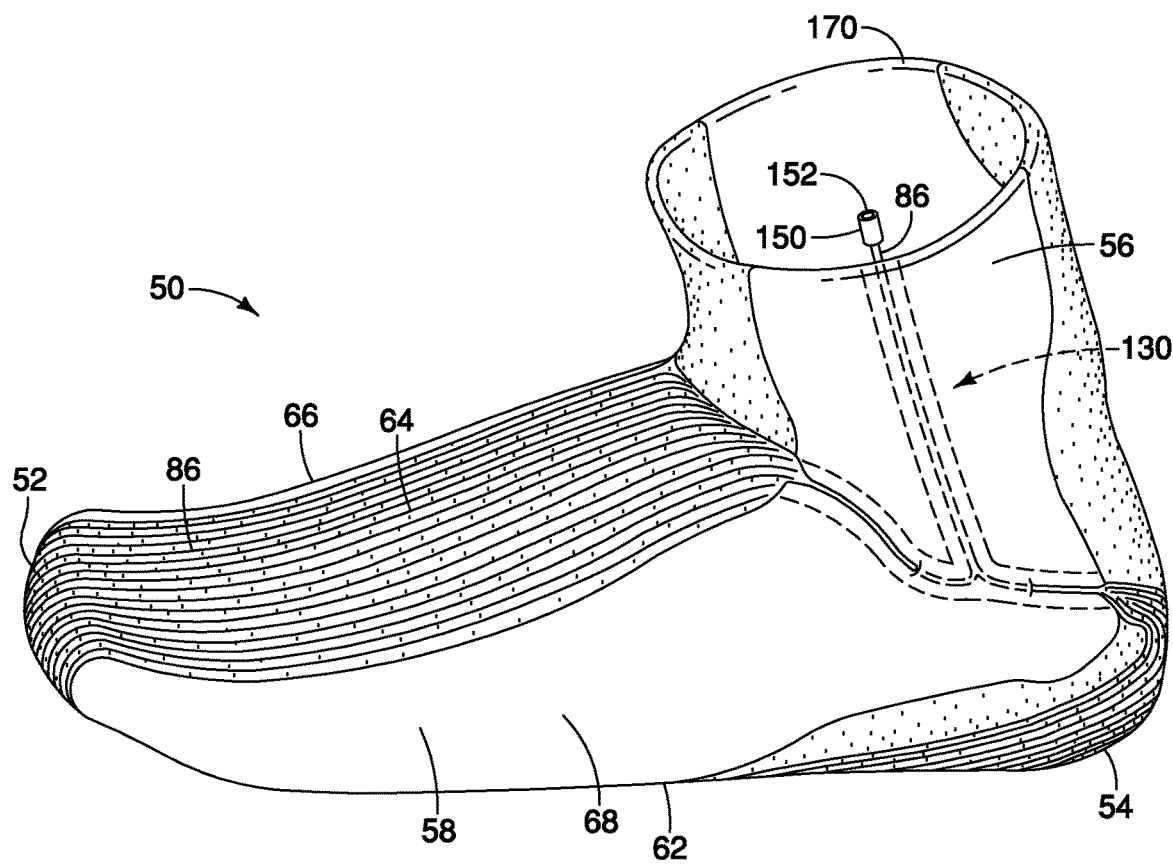
FIG. 1 is a schematic perspective view of an illuminated sock.

FIG. 1 depicts a garment in the form of a sock 50 that is configured to project light toward a targeted body area of a person wearing the sock 50. For example, light having a wave length between 630 nm and 900 nm has been found beneficial to increase blood flow, may provide ameliorative effects with regard to inflammation, and can be beneficial in the treatment of diabetic neuropathy, and as such can be referred to as light having a therapeutic wave length. The sock 50 depicted in FIG. 1 is only one example of a garment configured to project light toward a targeted body area of a person. Other such garments can include shirts, shorts, pants, gloves, etc. to target body areas that can include muscle, muscle groups, joints, and human extremities, such as the foot and genetalia, as examples. The sock 50, as well as the other aforementioned garments, can also be configured to project light at wave lengths other than between 630 nm and 900 nm, which also may have a therapeutic effect.

The sock 50 is designed to be worn by a person in a similar manner as a conventional sock, e.g., worn over the person's foot and lower leg. Similar to conventional socks, the sock 50 depicted in FIG. 1 includes a toe region 52, a heel region 54, and a leg region 56. The toe region 52 receives a person's toes when the sock 50 is worn. The heel region 54 covers the person's heel, and the leg region 56 receives the person's lower leg. The sock 50 also includes a foot region 58, which accommodates the wearer's foot, and the foot region 58 can be further separated into a sole zone 62 positioned along the sole of a person's foot when wearing the sock, a top zone 64 positioned along the top of the person's foot when wearing the sock, an interior lateral zone 66, and an exterior lateral zone 68, which are on the sides of the person's foot when wearing the sock. At an opposite end as compared to the toe region 52, the sock 50 terminates with a cuff 70, which can include a more elastic section to help keep the sock in place.

Figure 2:
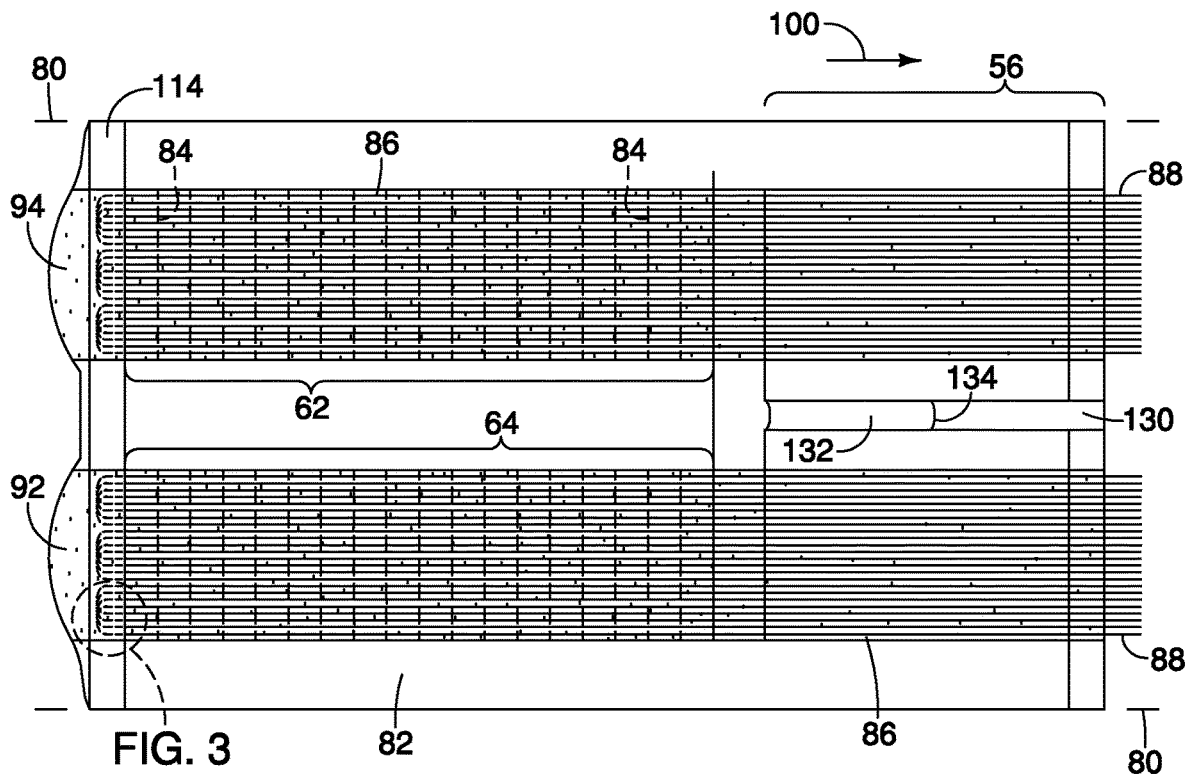
FIG. 2 is a plan view of the illuminated sock of FIG. 1 deconstructed along a match line to show an inner side of the illuminated sock prior to bundling optical fibers and inserting the bundled optical fibers into a tunnel.

FIG. 2 shows the sock 50 in deconstructed in a manner. When the sock 50 is finally assembled, the sock 50 is folded over such that match lines 80 meet. A seam can be provided where the match lines 80 meet, or the sock 50 can be knitted in a tubular fashion that would allow the seam at the match line 80 to be omitted. The sock 50 includes a knitted fabric base layer 82 formed from a yarn or a plurality of yarns that provides a comfort component for the sock 50. Examples of such yarn can include wool, silk, cotton, polyester, cotton/polyester blends, microdenier polyester/cotton blends, and combinations thereof. The yarn can also include an elastic fiber such as lycra or spandex, and more than one type of yarn can form the fabric base layer 82.

The base layer 82 has knitted looped threads 84 that hold in position a plurality of optical fibers 86, which are laid into the base layer 82 during the same knitting cycle as the base layer 82. The optical fibers 86 differ from the yarn that makes up the base layer 82 and the knitted looped threads 84, which are made from the same yarn as the base layer 82, in that the optical fibers 86 are configured to emit light through respective sides and along the length of each optical fiber 86. An outer diameter of each optical fiber 86 can be between about 0.25 mm and about 0.75 mm, which is larger than an outer diameter of the yarn from which the base layer 82 is knitted. At least a majority, and preferably all, of the plurality of optical fibers 86 are cut at each end 88 and receive light from a light source 90 (see FIG. 4) at each end 88. The light emitted from the light source 90 can have a wave length between 630 nm and 900 nm so as to provide a therapeutic wave length to a wearer of the sock 50. The light emitted from the light source 90, however, can be at wave lengths other than between 630 nm and 900 nm, which also may have a therapeutic effect.

Each optical fiber 86 is aligned substantially parallel to a direction of donning (see arrow 100) of the sock 50 along at least a majority of a length of each respective optical fiber 86 that is held in position by the knitted looped threads 84. The sock 50 is pulled in the direction of donning (arrow 100) when being put on by the wearer. More particularly, each optical fiber 86 within the sole zone 62 and the top zone 84 of the foot region 58 is aligned substantially parallel to the direction of donning (arrow 100) of the sock 50. Such an orientation of the optical fibers 86 facilitates donning of the sock 50 while inhibiting accidental snagging of the optical fibers 86 while the sock 50 is being donned.

Figure 3:
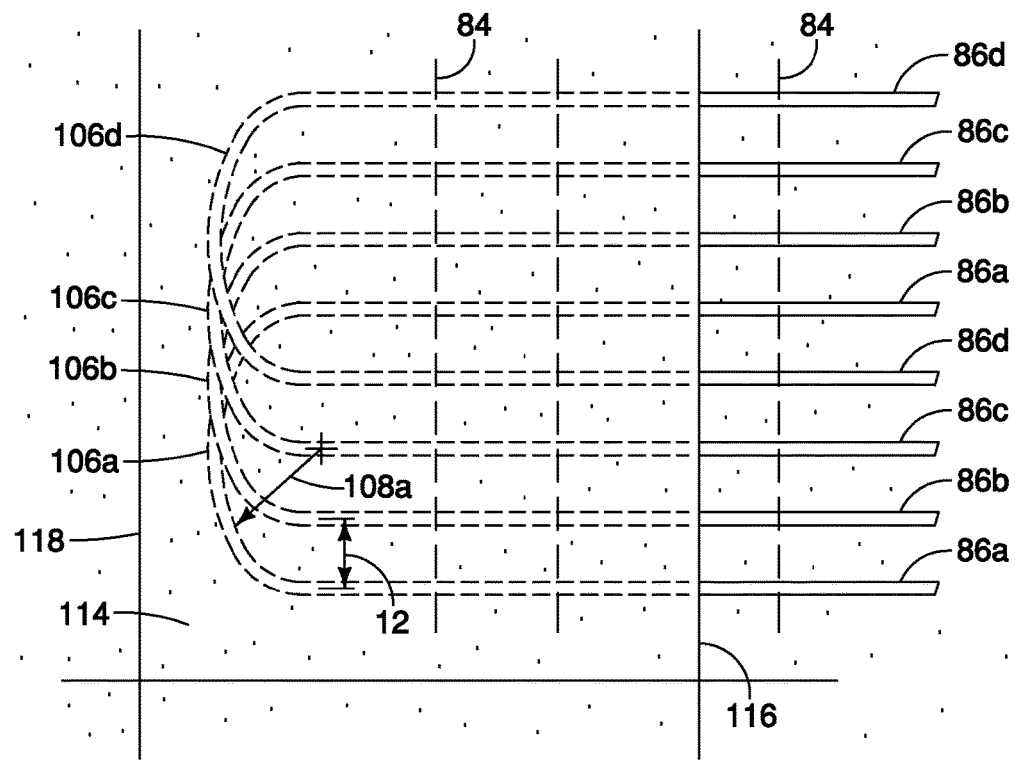
FIG. 3 is a close-up view of a circled portion of FIG. 2.

FIG. 3 depicts a close-up view of an upper toe section 92, which is part of the toe region 52 of the sock 50. The upper toe section 92 covers the toenails of the wearer of the sock 50 when worn. A lower toe section 94, which is visible in FIG. 2 and covers the lower surface of the wearer's toes, has a similar construction and the upper toe section 92 will be described in particularity with respect to FIG. 3 with the understanding that the lower toe section 94 has a similar construction. Each optical fiber 86a, 86b, 86c, 86d includes a respective loop 106a, 106b, 106c, 106d positioned within the toe region 52 of the sock 50. Each loop 106a, 106b, 106c, 106d has a radius (only radius 108a is shown in FIG. 3 for purposes of clarity) that is greater than spacing 112 (only spacing between optical fibers 86a and 86b is shown in FIG. 3 for purposes of clarity) between adjacent optical fibers along portions of the respective optical fibers aligned substantially parallel to a direction on donning of the sock 50. In the illustrated embodiment, the radius 108a is greater than the spacing 112 between adjacent optical fibers 86 along portions of the respective optical fibers located within the foot region 58 of the sock 50. This results in the optical fibers 86a, 86b, 86c, 86d being "cascaded" in that the first optical fiber 86a crosses over optical fibers 86b, 86c, and 86d. Similarly, the second optical fiber 86b crosses over optical fibers 86a, 86c, and 86d, and so on.

The knitted looped threads 84 hold the optical fibers 86 in position so as to maintain the desired spacing 112, which can be less than about 6.35 mm. The knitted looped threads 84, however, need not preclude movement of the respective optical fibers 86 with respect to the base layer 82 in the direction of donning (arrow 100), e.g., along the length of the optical fibers 86.

The toe region 52 is constructed so as to have a double layer construction. Each loop 106a, 106b, 106c and 106d is positioned between opposing layers of the double layer construction so that a toe tunnel 114 is provided in the toe region 52. The double layer construction in the toe region 52 is open at an edge 116 adjacent the foot region 58 to receive the plurality of optical fibers between the opposing layers. A distal seam 118 is provided where the opposing layers of the double layer construction are connected. The distal seam 118 can limit movement of the optical fibers 86 with respect to the base layer 82. For example, if one end of the first optical fiber 86a is pushed in a direction opposite that of the direction of donning (arrow 100), the loop 106a would want to travel toward the distal seam 118. This is because the knitted looped threads 84 hold the optical fibers 86 in position so as to maintain the desired spacing 112, and do not preclude movement of the respective optical fibers 86 with respect to the base layer 82 in a direction parallel to the direction of donning (arrow 100). If the loop 106a were to come into contact with the distal seam 118, further travel of the first optical thread 86a parallel to and opposite that of the direction of donning would be precluded.

In the illustrated embodiment, each lateral zone, i.e., the interior lateral zone 66 and the exterior lateral zone 68, is configured to stretch more than each of the sole zone 62 and the top zone 64. When making the sock 50, the interior lateral zone 66 and the exterior lateral zone 68 can be knitted so that the base layer 82 is knitted from yarns that include elastic fibers, such as lycra and spandex, while the sole zone 62 and the top zone 64 can be knitted so that the base layer 82 is knitted from yarns that are not as elastic, e.g., wool, silk and cotton. In the illustrated embodiment, the optical fibers 86 are only inlaid into the sole zone 62 and the top zone 64, which are made from a relatively more comfortable yarn. The interior lateral zone 66 and the exterior lateral zone 68 in the foot region 58, however, are devoid of the optical fibers 86.

Figure 4:
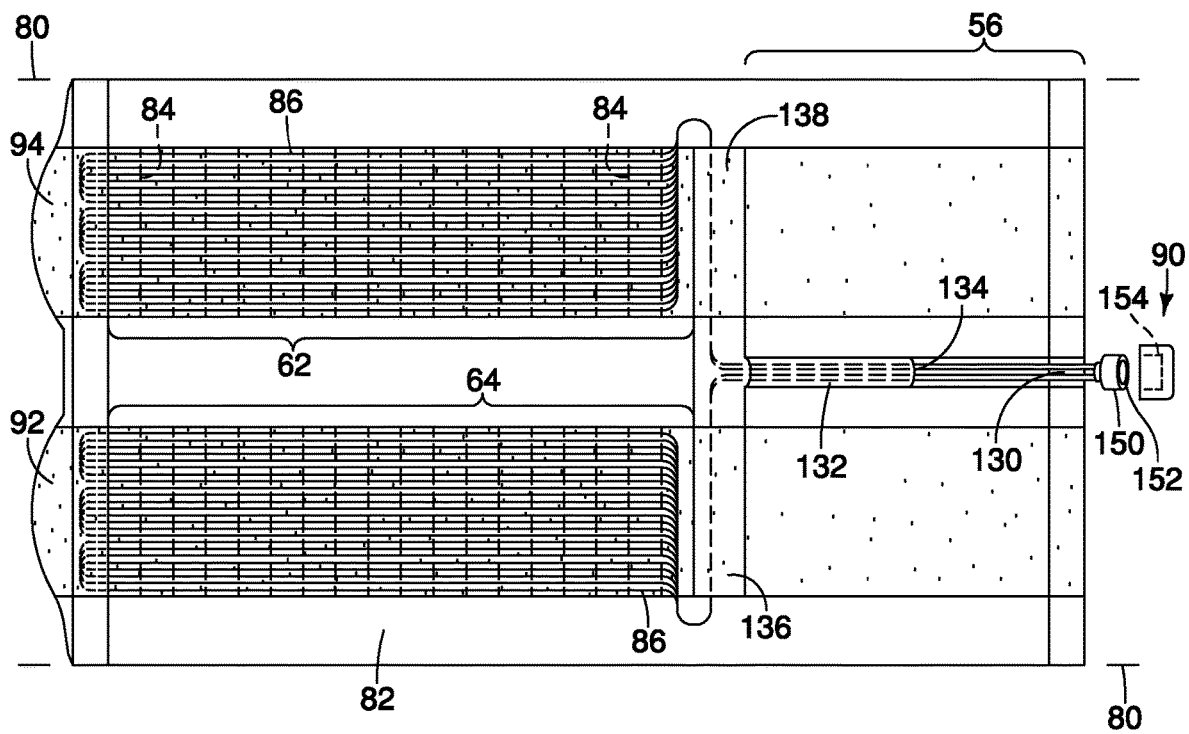
FIG. 4 is a plan view of the illuminated sock of FIG. 1 deconstructed along the match line to show the inner side of the illuminated sock after bundling the optical fibers and inserting the bundled optical fibers into the tunnel.

With reference to FIG. 4, the leg region 56 includes a double layer construction to define a leg tunnel 130 in the leg region 56. The plurality of optical fibers 86 are routed through the leg tunnel 130 and terminate adjacent the cuff 70. The leg tunnel 130 is T-shaped in the illustrated embodiment having a main branch 132 that extends from the cuff 70 toward the foot region 58 in the interior lateral zone 68 of the leg region 56. An opening 134, e.g. a slit, is provided in the main branch 132 spaced from the cuff 70. The plurality of optical fibers 86 can exit the tunnel 130 through the opening 134 prior to connecting with the light source 90. The tunnel 130 also includes branches, such as an upper branch 136 and a lower branch 138. The upper branch 136 extends from the main branch 132 towards the top zone 64 in the foot region 58. The lower branch 138 extends from the main branch 132 towards the sole zone 62 in the foot region 58. The optical fibers 86 from the top zone 64 enter the upper branch 136 and are bent towards the main branch 132, and the optical fibers 86 from the sole zone 62 enter the lower branch 138 and are bent towards the main branch 132. The optical fibers 86 when in the tunnel 130 are positioned between opposing layers of the double layer construction of the tunnel 130. The optical fibers 86 can be bundled within the main branch 134 prior being received in a light source connector 150.

The light source connector 150 can be made from a magnetic material. In the illustrated embodiment, the light source connector 150 is cylindrical in configuration having a central passage 152 that receives the optical fibers 86. The light source connector 150 can be another axially symmetric shape so that the light source connector 150 is configured to connect with the light source 90 in a plurality of different rotational orientations with respect to a central axis of the light source connector 150. This allows for ease of installation in that a socket 154 in the light source 90, which can also be made from a metallic material, can be brought close to the light source connector 150, or vice versa, and the magnetic attraction between the light source connector 150 and the socket 154 can finish the connection. By providing an axially symmetric light source connector 150, the orientation between the light source connector 150 and the socket 154 is not critical.

Figure 5:
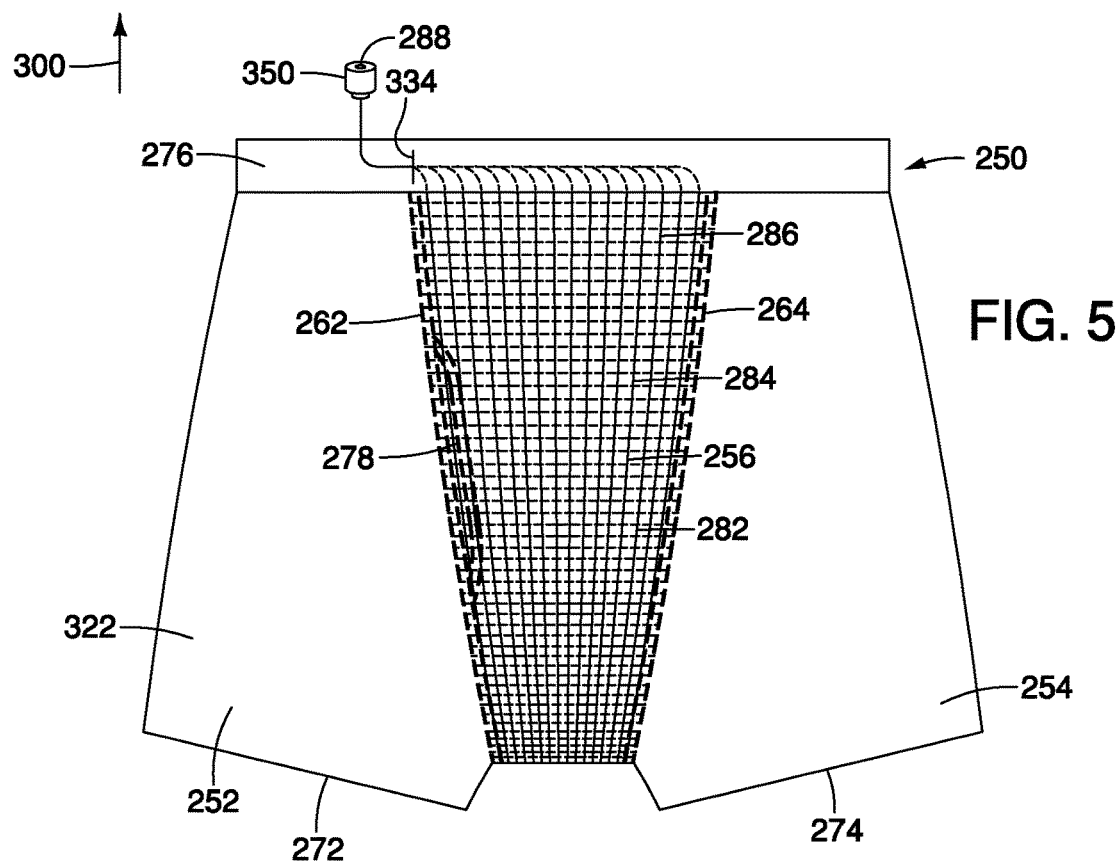
FIG. 5 is a front view of men's briefs.
Figure 6:
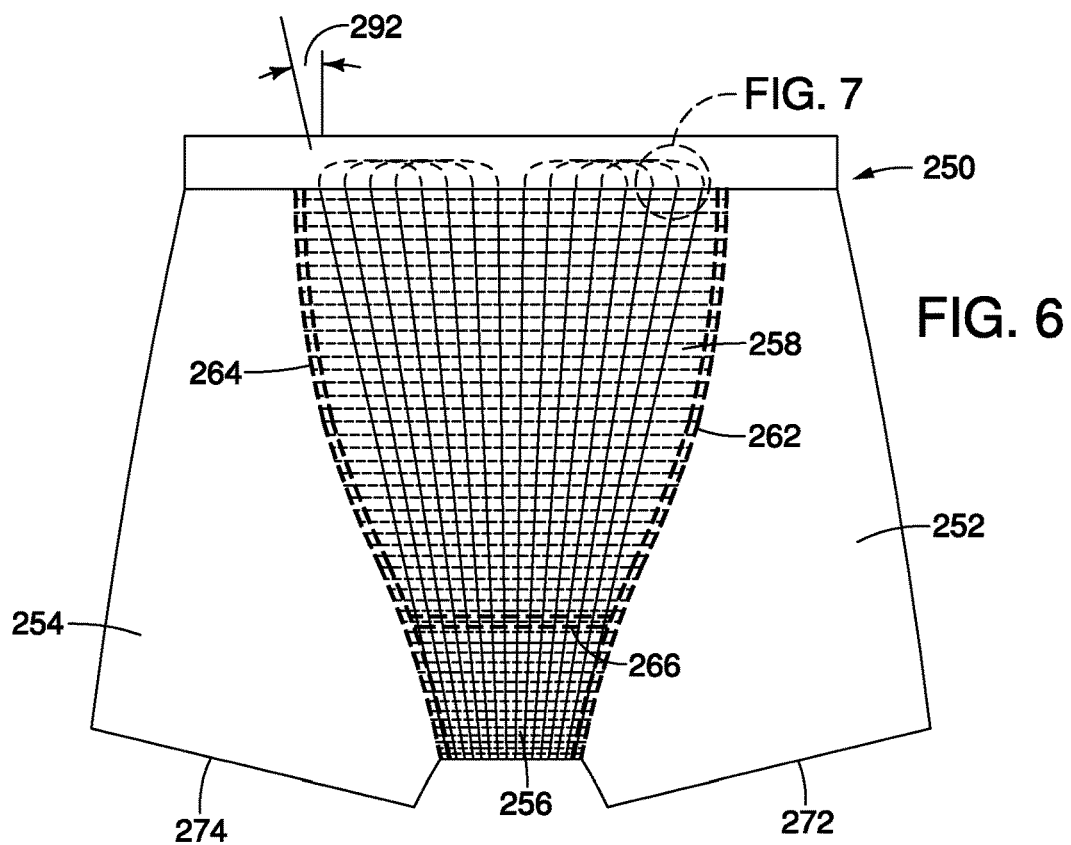
FIG. 6 is a rear view of the men's briefs depicted in FIG. 5.

FIGS. 5 and 6 depict a garment in the form of a men's briefs 250 that are configured to project light toward a targeted body area, e.g. genitalia, of a person wearing the men's briefs 250. Similar to the sock 500 described above, the men's briefs 250 can be configured to project light at a particular wave length, e.g. between 630 nm and 900 nm, or at wave lengths other than between 630 nm and 900 nm, which also may have a therapeutic effect.

The men's briefs 250 are designed to be worn by a person in a similar manner as conventional men's briefs, e.g. worn over the person's groin and buttocks. Similar to conventional men's briefs, the men's briefs 250 depicted in FIGS. 5 and 6 include a right leg portion 252 and a left leg portion 254. At least one gusset, which includes a front gusset 256 and a rear gusset 258 in the illustrated embodiment, is positioned between the right leg portion 252 and the left leg portion 256. A right inseam 262 connects the right leg portion 252 with the front gusset 256 and the rear gusset 258. A left inseam 264 connects the left leg portion 254 with the front gusset 256 and the rear gusset 258. With reference to FIG. 6, a cross seam 266 connects the front gusset 256 and the rear gusset 258. The right leg portion 252 and the left leg portion 256 extend down onto the thigh region of the person wearing the men's briefs 250. The right leg portion 252 includes a right leg opening 272 to accommodate the person's right leg, and the left leg portion 254 includes a left leg opening 274 to accommodate the person's left leg. The leg portions 252, 254 extend onto the thigh such that the men's briefs 250 are shown as what may be referred to as men's boxer briefs. The leg portions 252, 254 can also be shortened from that shown in FIGS. 5 and 6. Both types of briefs, men's boxer briefs and men's briefs having shorter legs, are intended to be encompassed by the term "men's briefs." The men's briefs 250 can also include a waistband 276 and a fly 278.

The gussets 256, 258 includes a knitted fabric base layer 282 formed from a yarn or a plurality of yarns that provides a comfort component for the gussets 256, 258. Examples of such yarn can include wool, silk, cotton, polyester, cotton/polyester blends, microdenier polyester/cotton blends, and combinations thereof. The yarn can also include an elastic fiber such as lycra or spandex, and more than one type of yarn can form the fabric base layer 282.

The base layer 282 has knitted looped threads 284 that hold in position a plurality of optical fibers 286, which can be laid into the base layer 282 during the same knitting cycle as the base layer 282. The optical fibers 286 differ from the yarn that makes up the base layer 282 and the knitted looped threads 284, which are made from the same yarn as the base layer 282, in that the optical fibers 286 are configured to emit light through respective sides and along the length of each optical fiber 286. An outer diameter of each optical fiber 286 can be between about 0.25 mm and about 0.75 mm, which is larger than an outer diameter of the yarn from which the base layer 282 is knitted. At least a majority, and preferably all, of the plurality of optical fibers 286 are cut at each end 288 and receive light from a light source (not shown, but similar to the light source 90 shown in FIG. 4) at each end 288. The light emitted from the light source can have a wave length between 630 nm and 900 nm so as to provide a therapeutic wave length to a wearer of the men's briefs 250. The light emitted from the light source 90, however, can be at wave lengths other than between 630 nm and 900 nm, which also may have a therapeutic effect.

Each optical fiber 286 is aligned angularly offset an internal angle 292 of less than 45 degrees with respect to a direction of donning (see arrow 300) of the men's briefs 250 along at least a majority of a length of each respective optical fiber 286 that is held in position by the knitted looped threads 284. The men's briefs 250 is pulled in the direction of donning (arrow 300) when being put on by the wearer. More particularly, each optical fiber 86 within the gussets 256, 258 is aligned angularly offset an internal angle 292 of less than 20 degrees with respect to the direction of donning (arrow 300) of the men's briefs 250. Such an orientation of the optical fibers 286, i.e., closer to vertical than to horizontal as shown in FIGS. 5 and 6, facilitates donning of the men's briefs 250 while inhibiting accidental snagging of the optical fibers 286 while the men's briefs 250 is being donned.

Figure 7:
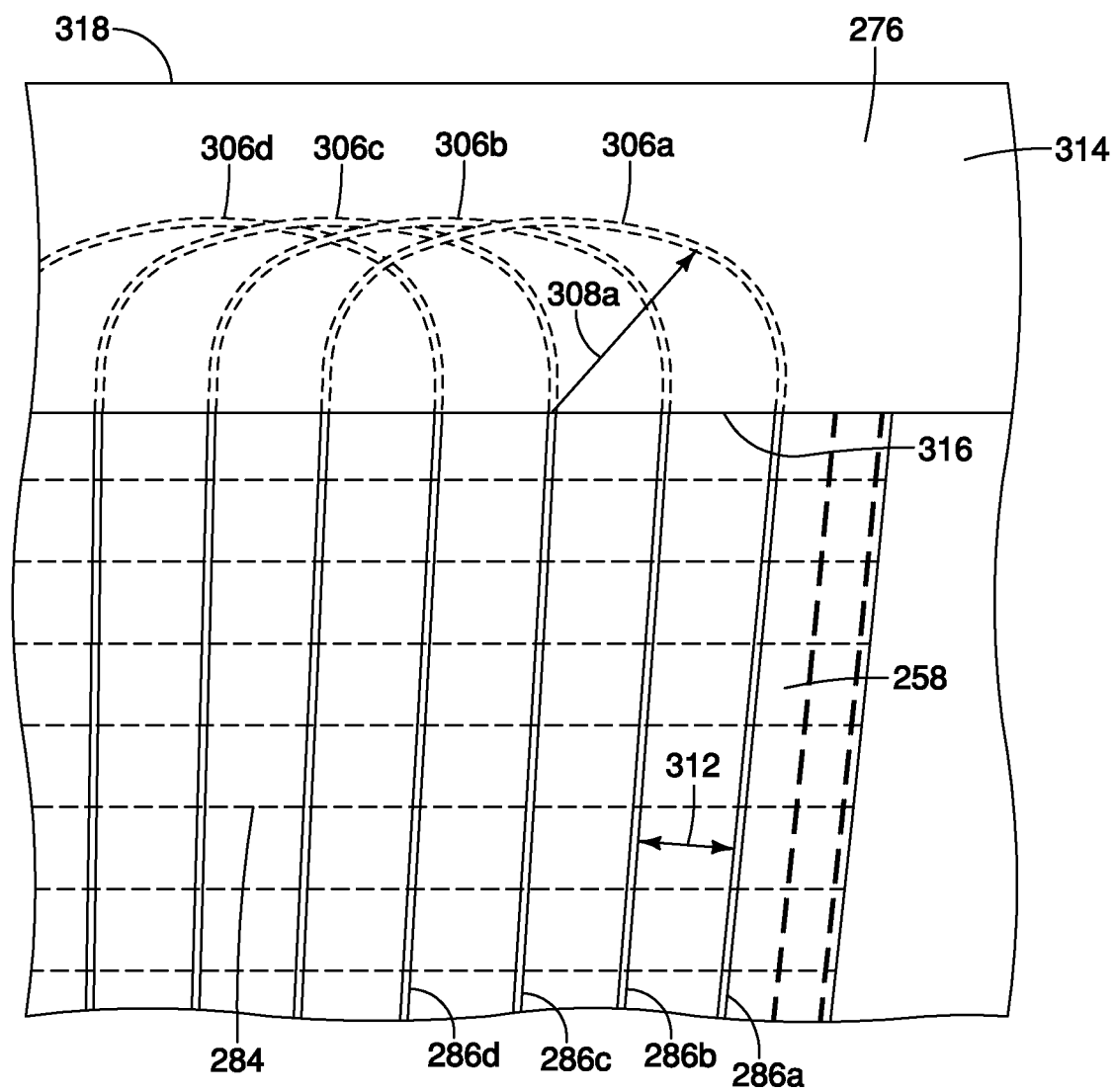
FIG. 7 is a close-up view of a circled portion of FIG. 6.

FIG. 7 depicts a close-up view of a portion of the waistband 276. Each optical fiber 286a, 286b, 286c, 286d includes a respective loop 306a, 306b, 306c, 306d positioned within waistband 276. Each loop 306a, 306b, 306c, 306d has a radius (only radius 308a is shown in FIG. 7 for purposes of clarity). Each radius is greater than spacing 312 (only spacing between optical fibers 286a and 286b is shown in FIG. 7 for purposes of clarity) between adjacent optical fibers along portions of the respective optical fibers 286a, 286b, 286c, 286d aligned angularly offset an internal angle 292 of less than 20 degrees with respect to the direction of donning (arrow 300) of the men's briefs 250. In the illustrated embodiment, the radius 308a is greater than the spacing 312 between adjacent optical fibers 386 along portions of the respective optical fibers located within the within the gussets 256, 258. This results in the optical fibers 286a, 286b, 286c, 286d being "cascaded" within the waistband 276 in that the first optical fiber 286a crosses over optical fibers 286b, 286c, and 286d. Similarly, the second optical fiber 286b crosses over optical fibers 286a, 286c, and 286d, and so on.

The knitted looped threads 284 hold the optical fibers 286 in position so as to maintain the desired spacing 312, which can be less than about 6.35 mm. The knitted looped threads 284, however, need not preclude movement of the respective optical fibers 286 with respect to the base layer 282 in the direction angularly offset an internal angle 292 with respect to the direction of donning (arrow 300), e.g., along the length of the optical fibers 286.

The waistband 276 is constructed so as to have a double layer construction. Each loop 306a, 306b, 306c and 306d is positioned between opposing layers of the double layer construction so that a waistband tunnel 314 is provided in the waistband 276. The double layer construction in the waistband 276 is open at an edge 316 where the waistband 276 meets the gussets 256, 258 to receive the plurality of optical fibers 286 between the opposing layers. A distal seam 318 is provided at a top edge of the waistband 276 where the opposing layers of the double layer construction are connected. The distal seam 318 can limit movement of the optical fibers 286 with respect to the base layer 282 in a similar manner that the seam 118 in the sock 50 limits movement of the optical fibers 86 with respect to the base layer 82 of the sock 50.

In the illustrated embodiment, each leg portion, i.e., the right leg portion 252 and the left leg portion 254, is configured to stretch more than gussets 256, 258. When making the men's brief 250, the right leg portion 252 and the left leg portion 254 can be knitted so that each portion's base layer 322 is knitted from yarns that include elastic fibers, such as lycra and spandex, while the gussets 256, 258 can be knitted so that the base layer 282 is knitted from yarns that are not as elastic, e.g., wool, silk and cotton. In the illustrated embodiment, the optical fibers 286 are only inlaid into the gussets 256, 258, which are made from a relatively more comfortable yarn. The leg portions 252, 254, however, are devoid of the optical fibers 286.

With reference to FIG. 6, the waistband 276 includes the double layer construction to define the waistband tunnel 314 (see also FIG. 7). The plurality of optical fibers 286 are routed through the waistband tunnel 314 and extend through an opening 334, e.g. a slit, provided in the waistband tunnel 314. The plurality of optical fibers 286 can exit the waistband tunnel 314 through the opening 334 and be bundled prior to being received in a light source connector 350, which can be cylindrical and made from a magnetic material similar to the light source connector 150 described above. The light source connector 150 can cooperate with a light source similar to the light source 90 described above.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. An illuminated garment comprising a base layer having knitted looped threads that hold in position a plurality of optical fibers, which are laid into the base layer during the same knitting cycle as the base layer and are configured to emit light through the respective sides and along the length of each optical fiber of the plurality of optical fibers in response to receiving light from a light source through at least one end of the respective optical fibers, wherein the garment is a sock comprising a foot region including a sole zone positioned along the sole of a person's foot when wearing the sock, a top zone positioned along the top of the person's foot when wearing the sock, an interior lateral zone and an exterior lateral zone, wherein each lateral zone is configured to stretch more than each of the sole zone and the top zone, wherein the plurality of optical fibers are inlaid into each of the sole zone and the top zone, wherein the sock further includes a leg region, wherein the leg region includes a double layer construction to define a leg tunnel in the leg region, wherein the plurality of optical fibers are routed through the leg tunnel and terminate adjacent a cuff.

2. The illuminated garment of claim 1, wherein each optical fiber is aligned substantially parallel to a direction of donning of the sock in each of the sole zone and the top zone.

3. The illuminated garment of claim 1, wherein the plurality of optical fibers are bundled together and are routed through the leg tunnel in a bundle.

4. An illuminated garment comprising a base layer having knitted looped threads that hold in position a plurality of optical fibers, which are laid into the base layer during the same knitting cycle as the base layer and are configured to emit light through the respective sides and along the length of each optical fiber of the plurality of optical fibers in response to receiving light from a light source through at least one end of the respective optical fibers, wherein the garment is men's briefs comprising a right leg portion, a left leg portion, at least one gusset positioned between the right leg portion and the left leg portion, and a waistband, wherein each lateral leg portion is configured to stretch more than the at least one gusset, wherein the plurality of optical fibers are inlaid into the at least one gusset, wherein the men's briefs further include a double layer construction in the waistband to define a waistband tunnel, wherein the plurality of optical fibers are routed through the waistband tunnel.

5. The illuminated garment of claim 4, wherein each optical fiber is aligned angularly offset an internal angle of less than 20 degrees with respect to the direction of donning of the garment in the at least one gusset.

* * * * *